United States Patent
Lee et al.

(10) Patent No.: US 9,150,601 B2
(45) Date of Patent: Oct. 6, 2015

(54) BLUE-LIGHT-EMITTING IRIDIUM COMPLEX, IRIDIUM COMPLEX MONOMER, PHOSPHORUS POLYMER, AND ORGANIC ELECTROLUMINESCENCE DEVICE USING SAME

(75) Inventors: Jae-Suk Lee, Gwangju (KR); Nam-Goo Kang, Gwangju (KR)

(73) Assignee: GWANGJU INSTITUTE OF SCIENCE AND TECHNOLOGY, Gwangju (KR)

(*) Notice: Subject to any disclaimer, the term of this patent is extended or adjusted under 35 U.S.C. 154(b) by 900 days.

(21) Appl. No.: 13/389,697

(22) PCT Filed: Aug. 10, 2010

(86) PCT No.: PCT/KR2010/005218
§ 371 (c)(1),
(2), (4) Date: Feb. 9, 2012

(87) PCT Pub. No.: WO2011/019179
PCT Pub. Date: Feb. 17, 2011

(65) Prior Publication Data
US 2012/0138917 A1 Jun. 7, 2012

(30) Foreign Application Priority Data
Aug. 12, 2009 (KR) .................. 10-2009-0074160

(51) Int. Cl.
*C07F 15/00* (2006.01)
*H01L 51/50* (2006.01)
*C08F 130/04* (2006.01)
*C08F 220/36* (2006.01)
*C09K 11/06* (2006.01)

(52) U.S. Cl.
CPC ........... *C07F 15/004* (2013.01); *C07F 15/0033* (2013.01); *C08F 130/04* (2013.01); *C08F 220/36* (2013.01); *C09K 11/06* (2013.01); *C09K 2211/1029* (2013.01); *C09K 2211/1059* (2013.01); *C09K 2211/1466* (2013.01); *C09K 2211/185* (2013.01)

(58) Field of Classification Search
USPC ............................................... 546/2; 313/504
See application file for complete search history.

(56) References Cited

U.S. PATENT DOCUMENTS

| 2002/0134984 A1* | 9/2002 | Igarashi .................... 257/79 |
| 2007/0085073 A1 | 4/2007 | Inoue et al. |
| 2007/0141394 A1 | 6/2007 | Cheng et al. |

FOREIGN PATENT DOCUMENTS

| JP | 2007-123392 A | 5/2007 |
| JP | 2007-258550 A | 10/2007 |
| JP | 2007-294720 A | 11/2007 |

OTHER PUBLICATIONS

Wu, L-L. et al.: Photophysical and electrochemical properties of blue phosphorescent iridium(III) complexes. Organometallics, vol. 26, pp. 2017-2023, 2007.*
International Search Report issued in PCT/KR2010/005218, mailed on Mar. 3, 2011, with translation, 4 pages.
Written Opinion issued in PCT/KR2010/005218, mailed on Mar. 3, 2011, 4 pages.
English Abstract of JP2007-294720 A, 1 page.

* cited by examiner

*Primary Examiner* — Charanjit Aulakh
(74) *Attorney, Agent, or Firm* — Osha Liang LLP

(57) ABSTRACT

Provided are a blue-light-emitting iridium complex, an iridium complex monomer, a phosphorescent polymer, and an organic electroluminescent device using same. The blue-light-emitting iridium complex contains a ligand having a low electron density structure, such as triazole or tetrazole. The iridium complex monomer containing a ligand having a polymerizable vinyl group produces a blue phosphorescent polymer through the polymerization with carbazole derivatives. The organic electroluminescent device comprises a first electrode, a second electrode, and a light-emitting layer interposed between the first electrode and the second electrode, wherein the light-emitting layer contains the above-described iridium complex or polymer containing the iridium complex.

4 Claims, 5 Drawing Sheets

Elution time (min)

ppm

BLUE-LIGHT-EMITTING IRIDIUM COMPLEX, IRIDIUM COMPLEX MONOMER, PHOSPHORUS POLYMER, AND ORGANIC ELECTROLUMINESCENCE DEVICE USING SAME

TECHNICAL FIELD

The present invention relates to an iridium complex and an organic electroluminescent device using the same and, more particularly, to a blue-light-emitting iridium complex, and a blue phosphorescent polymer and an organic electroluminescent device prepared using the same.

BACKGROUND ART

An electroluminescent device does not require a backlight, has a fast response speed, and also has excellent brightness and viewing angle characteristics as it is a self-light-emitting device. In particular, an organic electroluminescent device may be manufactured in the form of a thin film with a bendable structure. Moreover, the formation of patterns and the mass production by thin film manufacturing techniques are easy, and the driving voltage is low. Furthermore, the organic electroluminescent device can theoretically emit light of all colors in a visible light region. Thus, great efforts to develop light-emitting materials used in the organic electroluminescent devices have continued. However, since blue-light-emitting materials should have a wide band gap, it is difficult to synthesize and drive the blue-light-emitting materials compared to green and red-light-emitting materials. Therefore, in order to implement the organic electroluminescent device as a natural-color flat-panel display, it is necessary to continuously develop blue-light-emitting materials with improved efficiency, color, and stability.

DISCLOSURE

Technical Problem

A technical problem of the present invention is to provide a blue-light-emitting iridium complex and a blue phosphorescent polymer comprising the blue-light-emitting iridium complex and having improved stability and efficiency.

Another technical problem of the present invention is to provide an organic electroluminescent device comprising a blue-light-emitting iridium complex or a blue phosphorescent polymer containing the blue-light-emitting iridium complex.

Technical Solution

In one aspect, the present invention provides an iridium complex. The iridium complex may be an iridium complex represented by the following formula 1:

[Formula 1]

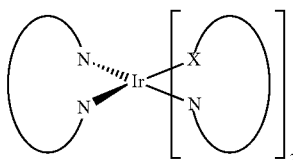

In the above formula 1,

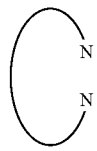

may be any one selected from the group consisting of compounds represented by the following formulas 2 to 5:

[Formula 2]

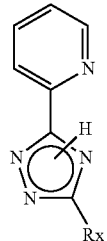

In the above formula 2, Rx may be hydrogen, a substituted or unsubstituted C1-C20 alkyl group, or a trifluoromethyl group;

[Formula 3]

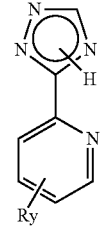

In the above formula 3, Ry may be hydrogen, a substituted or unsubstituted C1-C20 alkyl group, or an amine group (—NR'R", where R' and R" may be, independently from each other, hydrogen or a C1-C20 alkyl group);

[Formula 4]

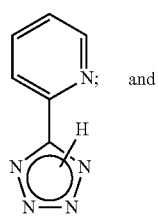

and

[Formula 5]

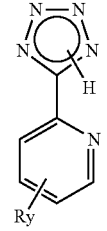

In the above formula 5, Ry may be hydrogen, a substituted or unsubstituted C1-C20 alkyl group, or an amine group (—NR'R", where R' and R" may be, independently from each other, hydrogen or a C1-C20 alkyl group).

In the above formula 1,

may be any one selected from the group consisting of compounds represented by the following formulas 6 to 8:

[Formula 6]

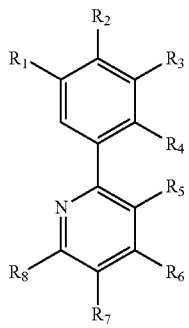

In the above formula 6, R1 to R4 may be, independently from each other, a fluorine group or a cyano group, and R5 to R8 may be, independently from each other, hydrogen, a substituted or unsubstituted C1-C20 alkyl group, a substituted or unsubstituted C1-C20 alkoxy group, or an amine group (—NR'R", where R' and R" may be, independently from each other, hydrogen or a C10-C20 alkyl group);

[Formula 7]

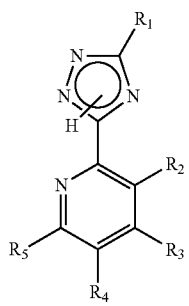

In the above formula 7, R1 may be hydrogen, a substituted or unsubstituted C1-C20 alkyl group, or a trifluoromethyl group, and R2 to R5 may be, independently from each other, hydrogen, a substituted or unsubstituted C1-C20 alkyl group, a substituted or unsubstituted C1-C20 alkoxy group, or an amine group (—NR'R", where R' and R" may be, independently from each other, hydrogen or a C1-C20 alkyl group); and

[Formula 8]

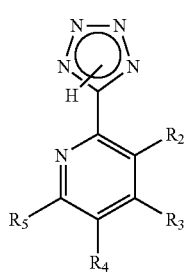

In the above formula 8, R1 to R4 may be, independently from each other, hydrogen, a substituted or unsubstituted C1-C20 alkyl group, a substituted or unsubstituted C1-C20 alkoxy group, or an amine group (—NR'R", where R' and R" may be, independently from each other, hydrogen or a C1-C20 alkyl group).

In another aspect, the present invention provides an iridium complex monomer. The iridium complex monomer may be a polymer represented by the following formula 9:

[Formula 9]

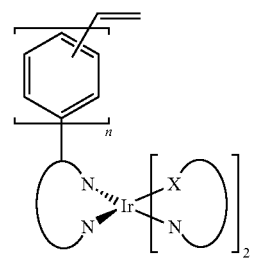

In the above formula 9, n may be an integer from 0 to 2, and

may be any one selected from the group consisting of the compounds represented by the above formulas 6 to 8.

Moreover,

may be any one selected from the group consisting of compounds represented by the following formulas 10 to 12:

[Formula 10]

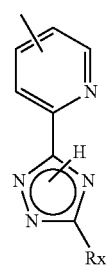

In the above formula 10, Rx may be hydrogen, a substituted or unsubstituted C1-C20 alkyl group, or a trifluoromethyl group;

[Formula 11]

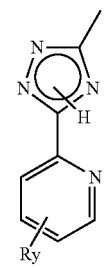

In the above formula 11, Ry may be hydrogen, a substituted or unsubstituted C1-C20 alkyl group, or an amine group (—NR'R", where R' and R" may be, independently from each other, hydrogen or a C1-C20 alkyl group); and

[Formula 12]

In still another aspect, the present invention provides an organic polymer comprising the above-described iridium complex. The polymer may be a polymer represented by the following formula 13:

[Formula 13]

In the above formula 13, R may be hydrogen or a substituted or unsubstituted C1-C20 alkyl group, $2 \leq x+y \leq 100$, and y is an integer from 1 to 99, A may be any one selected from the group consisting of carbazole derivatives represented by the following formulas 14 to 17, and B may be an iridium complex represented by the following formula 18:

[Formula 14]

[Formula 15]

[Formula 16]

[Formula 17]

and

[Formula 18]

In the above formula 18, n may be an integer from 0 to 2, and may be any one selected from the group consisting of the compounds represented by the above formulas 6 to 8.

Moreover, may be any one selected from the group consisting of compounds represented by the above formulas 10 to 12.

In yet another aspect, the present invention provides an organic electroluminescent device. The organic electroluminescent device comprises a first electrode, a second electrode disposed opposite to the first electrode, and a light-emitting layer interposed between the first electrode and the second electrode, and the light-emitting layer comprises the above-described iridium complex as a dopant or comprises the above-described polymer as a light-emitting material.

Moreover, the organic electroluminescent device may further comprise at least one of a hole transporting layer disposed between the first electrode and the light-emitting layer and an electron transporting layer disposed between the light-emitting layer and the second electrode.

ADVANTAGEOUS EFFECTS

As described above, according to the present invention, it is possible to increase the blue-light-emitting efficiency by synthesizing an iridium complex containing a ligand with a low electron density and to improve the stability and efficiency of an organic light-emitting material by polymerizing an iridium complex monomer containing a vinyl group with carbazole derivatives.

However, the effects of the present invention should not be limited to the foregoing description, and additional effects and advantages of the invention will be made more apparent to those skilled in the art from the following description.

MODE FOR INVENTION

Figure 1:
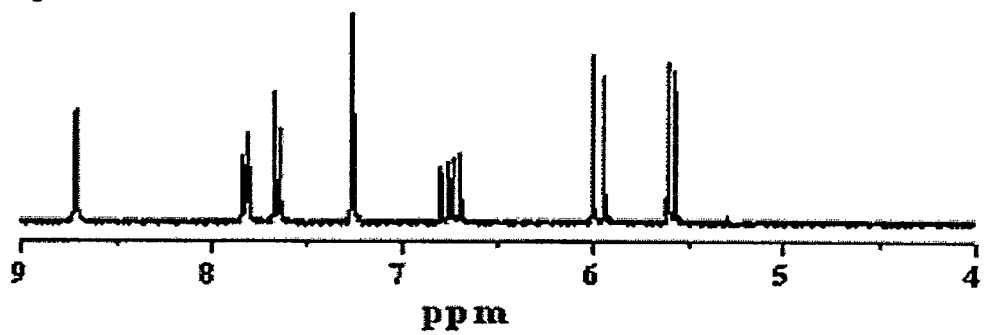
FIG. 1 shows a $^1$H-NMR spectrum of a 5-vinylpicolinonitrile intermediate prepared by reaction scheme 1.

Hereinafter, specific embodiments according to the present invention will be described with reference to the accompanying drawings. However, the present invention is not limited to the disclosed embodiments, but may be implemented in various manners. The embodiments are provided to complete the disclosure of the present invention and to allow those having ordinary skill in the art to understand the present invention. In the drawings, the thicknesses of layers and regions are exaggerated for clarity. The same reference numerals denote the same elements throughout the specification.

Example 1

Blue-Light-Emitting Iridium Complex

An iridium complex according to an exemplary embodiment of the present invention may be an iridium complex represented by the following formula 1:

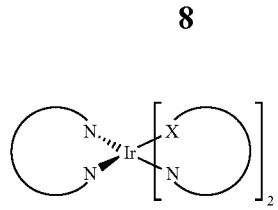

[Formula 1]

In the above formula 1,

may be any one selected from the group consisting of compounds represented by the following formulas 2 to 5:

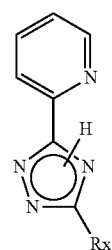

[Formula 2]

In the above formula 2, Rx may be hydrogen, a substituted or unsubstituted C1-C20 alkyl group, or a trifluoromethyl group;

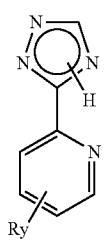

[Formula 3]

In the above formula 3, Ry may be hydrogen, a substituted or unsubstituted C1-C20 alkyl group, or an amine group (—NR'R", where R' and R" may be, independently from each other, hydrogen or a C1-C20 alkyl group);

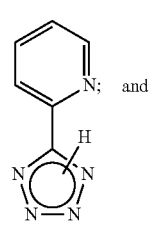

[Formula 4]

and

[Formula 5]

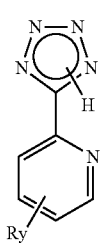

In the above formula 5, Ry may be hydrogen, a substituted or unsubstituted C1-C20 alkyl group, or an amine group (—NR'R", where R' and R" may be, independently from each other, hydrogen or a C1-C20 alkyl group).

Moreover, in the above formula 1,

may be any one selected from the group consisting of compounds represented by the following formulas 6 to 8:

[Formula 6]

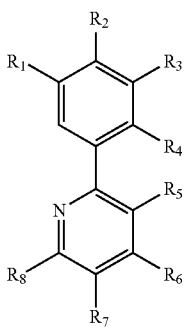

In the above formula 6, R1 to R4 may be, independently from each other, a fluorine group or a cyano group, and R5 to R8 may be, independently from each other, hydrogen, a substituted or unsubstituted C1-C20 alkyl group, a substituted or unsubstituted C1-C20 alkoxy group, or an amine group (—NR'R", where R' and R" may be, independently from each other, hydrogen or a C1-C20 alkyl group);

[Formula 7]

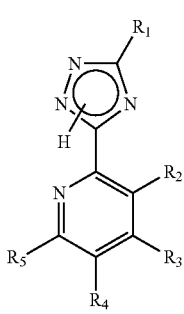

In the above formula 7, R1 may be hydrogen, a substituted or unsubstituted C1-C20 alkyl group, or a trifluoromethyl group, and R2 to R5 may be, independently from each other, hydrogen, a substituted or unsubstituted C1-C20 alkyl group, a substituted or unsubstituted C1-C2 alkoxy group, or an amine group (—NR'R", where R' and R" may be, independently from each other, hydrogen or a C1-C20 alkyl group); and

[Formula 8]

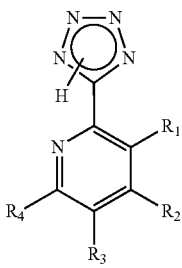

In the above formula 8, R1 to R4 may be, independently from each other, hydrogen, a substituted or unsubstituted C1-C20 alkyl group, a substituted or unsubstituted C1-C20 alkoxy group, or an amine group (—NR'R", where R' and R" may be, independently from each other, hydrogen or a C1-C20 alkyl group).

Example 2

Blue-Light-Emitting Iridium Complex Monomer

An iridium complex monomer according to another exemplary embodiment of the present invention may be an iridium complex monomer represented by the following formula 9:

[Formula 9]

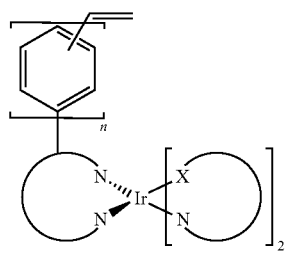

In the above formula 9, n may be an integer from 0 to 2, and

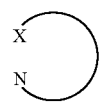

may be any one selected from the group consisting of the compounds represented by the above formulas 6 to 8.

Moreover,

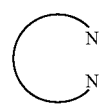

may be any one selected from the group consisting of compounds represented by the following formulas 10 to 12:

[Formula 10]

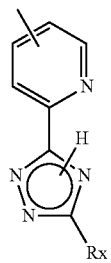

In the above formula 10, Rx may be hydrogen, a substituted or unsubstituted C1-C20 alkyl group, or a trifluoromethyl group;

[Formula 11]

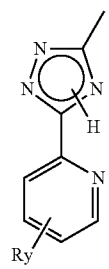

In the above formula 11, Ry may be hydrogen, a substituted or unsubstituted C1-C20 alkyl group, or an amine group (—NR'R", where R' and R" may be, independently from each other, hydrogen or a C1-C20 alkyl group); and

[Formula 12]

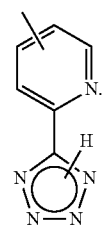

For example, the iridium complex monomer represented by the above formula 9 may be prepared by the following synthesis process:

[Synthesis process]

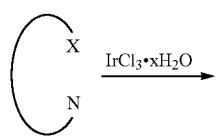

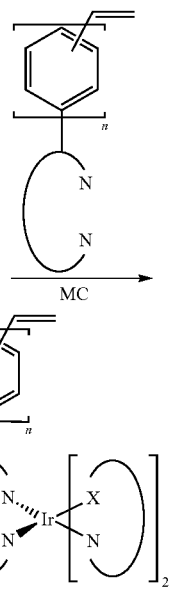

The iridium complex monomer of the above formula 9 is synthesized by reacting a ligand having no vinyl group with hydrated iridium trichloride ($IrCl_3 \cdot xH_2O$) to produce an intermediate in the form of a dinuclear with a chlorine atom via a ligand and then reacting the intermediate with a ligand having a vinyl group in the presence of a metal catalyst (MC).

Example 3

Blue-Light-Emitting Polymer Containing Iridium Complex

A polymer according to still another exemplary embodiment of the present invention may be a polymer represented by the following formula 13:

[Formula 13]

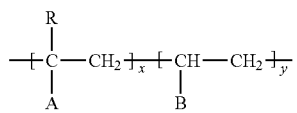

In the above formula 13, R may be hydrogen or a substituted or unsubstituted C1-C20 alkyl group, $2 \leq x+y \leq 100$, and y is an integer from 1 to 99, A may be any one selected from the group consisting of carbazole derivatives represented by the following formulas 14 to 17, and B may be an iridium complex represented by the following formula 18:

[Formula 14]

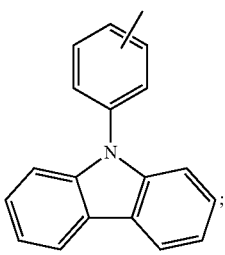

[Formula 15]

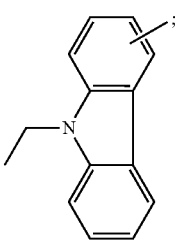

[Formula 16]

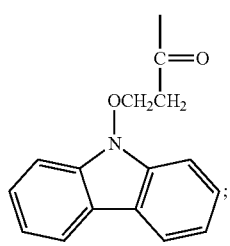

[Formula 17]

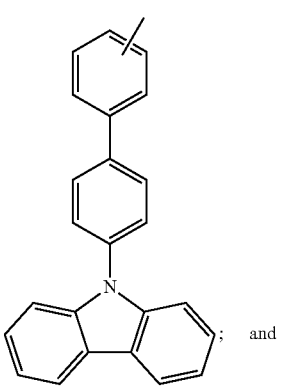
; and

[Formula 18]

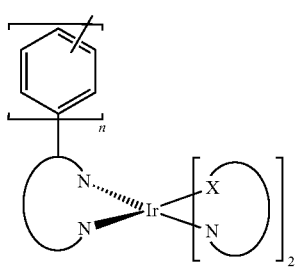

In the above formula 18, n may be an integer from 0 to and

may be any one selected from the group consisting of the compounds represented by the above formulas 6 to 8.

Moreover,

may be any one selected from the group consisting of compounds represented by the above formulas 10 to 12.

The polymer represented by the above formula 13 may be prepared by copolymerizing a carbazole derivative with an iridium complex monomer. For example, the copolymerization may be prepared by performing radical polymerization by adding a compound containing at least one selected from the group consisting of carbazole derivatives having a vinyl group and represented by the above formulas 14 to 17 in an organic solvent together with the iridium complex represented by the above formula 9 and a radical initiator. The radical initiator may include 2,2'-azo-bis(isobutyronitrile) (AIBN), benzoyl-peroxide (BM, etc., and the organic solvent may include tetrahydrofuran (THF), toluene, dioxane, xylene, etc.

Ligand Synthesis Example 1

Synthesis of 2-(4H-1,2,4-triazol-3-yl)-5-vinylpyridine

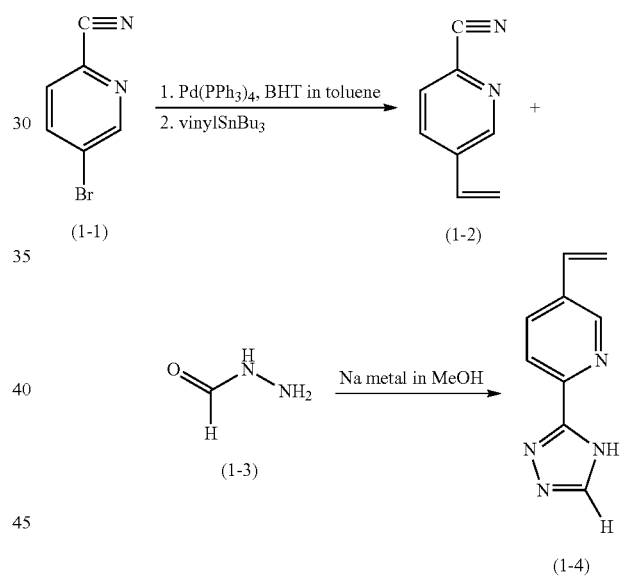

A 5-vinylpicolinonitrile intermediate (1-2) was prepared by adding 5-bromopicolinonitrile (1-1), tetrakis(triphenylphosphine) (Pd(PPH3)4), and 2,6-di-t-butyl-4-methylphenol (BHT) in toluene, adding tributyl(vinyl)stannane thereto, and reacting the resulting mixture at 80° C. for 24 hours. The intermediate (1-2) was added to a methanol solution, in which sodium metal was dissolved, and reacted at 70° C. for 3 hours and then cooled. Formohydrazide (1-3) was added to the reaction solution and reacted at 70° C. for 15 minutes. Then, the temperature was lowered to 25° C. and the reaction solution was reacted for 24 hours until yellow crystals were formed. Upon completion of the reaction, the yellow crystals were collected by filtration, and 2-(4H-1,2,4-triazol-3-yl)-5-vinylpyridine (1-4) was purified by column chromatography using chloroform and methanol as solvents.

FIG. 1 shows the $^1$H-NMR spectrum of the 5-vinylpicolinonitrile intermediate prepared by the above reaction scheme 1.

Figure 2:
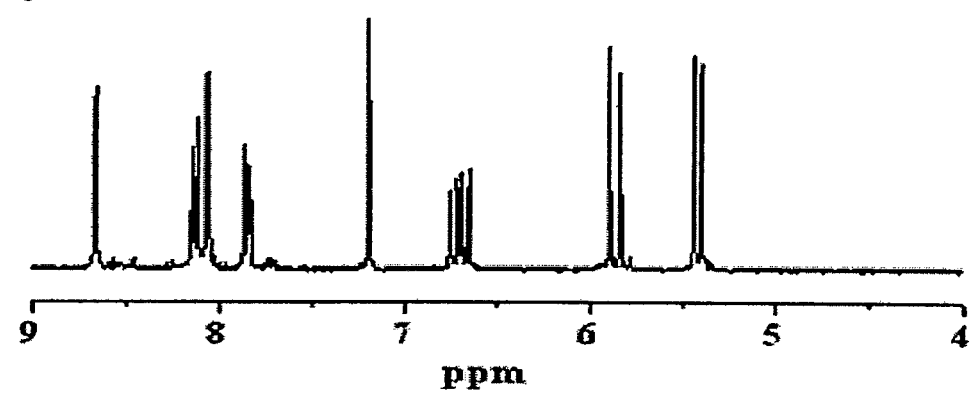
FIG. 2 shows a $^1$H-NMR spectrum of 2-(4H-1,2,4-triazol-3-yl)-5-vinylpyridine prepared by reaction scheme 1.

FIG. 2 shows the ¹H-NMR spectrum of the 2-(4H-1,2,4-triazol-3-yl)-5-vinylpyridine prepared by the above reaction scheme 1.

Ligand Synthesis Example 2

Synthesis of 2-(5-methyl-4H-1,2,4-triazol-3-yl)-5-vinylpyridine

[Reaction Scheme 2]

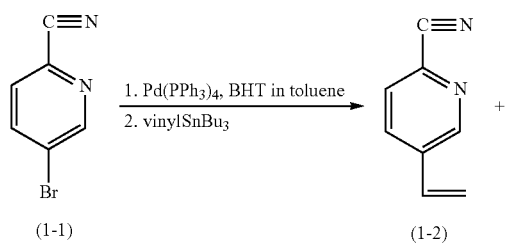

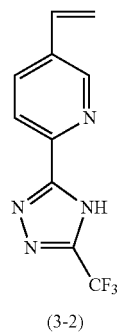

Synthesis was performed in the same manner described in the above reaction scheme 1 to purify 2-(5-methyl-4H-1,2,4-triazol-3-yl)-5-vinylpyridine (2-2), except that the compound that reacted with the 5-vinylpicolinonitrile intermediate (1-2) was acetohydrazide (2-1).

Ligand Synthesis Example 3

Synthesis of 2-(5-trifluoromethyl-4H-1,2,4-triazol-3-yl)-5-vinylpyridine

[Reaction Scheme 3]

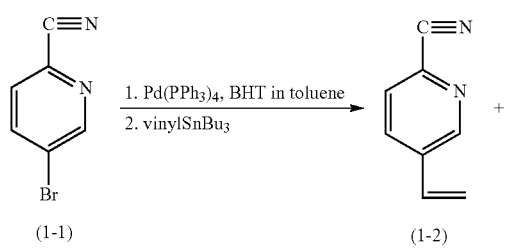

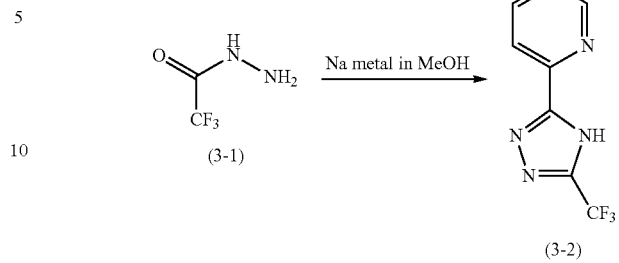

Synthesis was performed in the same manner described in the above reaction scheme 1 to purify 2-(5-trifluoromethyl-4H-1,2,4-triazol-3-yl)-5-vinylpyridine (3-2), except that the compound that reacted with the 5-vinylpicolinonitrile intermediate (1-2) was acetohydrazide (3-1).

Ligand Synthesis Example 4

Synthesis of 2-(1H-1,2,4-triazol-5-yl)-5-vinylpyridine

[Reaction Scheme 4]

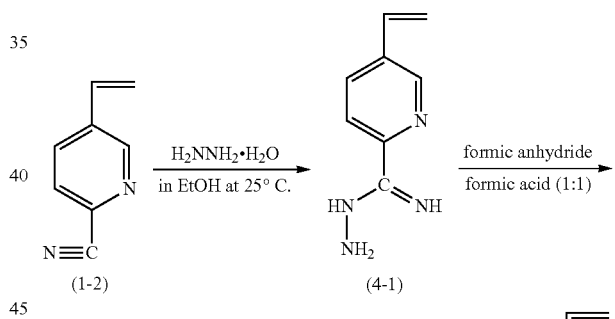

5-vinylpicolinimidohydrazine (4-1) was synthesized by adding the 5-vinylpicolinonitrile intermediate (1-2) to a methanol solution, in which hydrazine was dissolved, and reacted at 24° C. 2-(1H-1,2,4-triazol-5-yl)-5-vinylpyridine (4-2) was prepared by reacting the 5-vinylpicolinimidohydrazine (4-1) with a mixed solution of formic anhydride and formic acid (in a volume ratio of 1:1).

Ligand Synthesis Example 5

Synthesis of 2-(3-methyl-1H-1,2,3-triazol-5-yl)-5-vinylpyridine

[Reaction Scheme 5]

Synthesis was performed in the same manner described in the above reaction scheme 4 to prepare 2-(3-methyl-1H-1,2,3-triazol-5-yl)-5-vinylpyridine (5-1), except that a mixed solution of acetic anhydride and acetic acid was used as the reaction solution.

Ligand Synthesis Example 6

Synthesis of 2-(3-trifluoromethyl)-1H-1,2,4-triazol-5-yl)-5-vinylpyridine

[Reaction Scheme 6]

Synthesis is performed in the same manner described in the above reaction scheme 4 to prepare 2-(3-trifluoromethyl)-1H-1,2,4-triazol-5-yl)-5-vinylpyridine (6-1), except that a mixed solution of trifluoroacetic anhydride and trifluoroacetic acid was used as the reaction solution.

Ligand Synthesis Example 7

Synthesis of 2-(3-vinyl-1H-1,2-4-triazol-3-yl)pyridine

[Reaction Scheme 7]

Acrylohydrazide (7-2) was prepared by dissolving ethyl acrylate (7-1) and hydrazine in tetrahydrofuran (THF) and reacting the resulting solution at 80° C. for 1 hour. After the temperature of the resulting solution containing the acrylohydrazide (7-2) was lowered to room temperature, 2-amidino pyridine hydrochloride (7-3) and sodium hydroxide (NaOH) were added thereto and reacted at 80° C. for 1 hour, thereby preparing 2-(3-vinyl-1H-1,2-4-triazol-3-yl)pyridine (7-4). After the temperature was lowered to room temperature again, the reaction was terminated with sodium hydrogen carbonate (NaHCO$_3$) and then extracted with ethyl acetate. Then, purification was performed by column chromatography using hexane and ethyl acetate (1:1) as a solvent.

Ligand Synthesis Example 8

Synthesis of 4-methyl-2-(3-vinyl-1H-1,2,4-triazol-5-yl)pyridine

[Reaction Scheme 8]

-continued

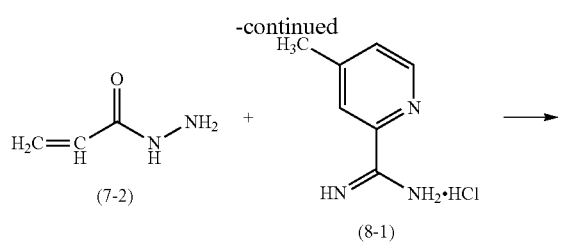

Synthesis was performed in the same manner described in the above reaction scheme 7 to purify 4-methyl-2-(3-vinyl-1H-1,2,4-triazol-5-yl)pyridine (8-2), except that 4-methylpicolinimidamide (8-1) was added to the reaction solution containing the acrylohydrazide (7-2).

Ligand Synthesis Example 9

Synthesis of 5-methyl-2-(3-vinyl-1H-1,2,4-triazol-5-yl)pyridine

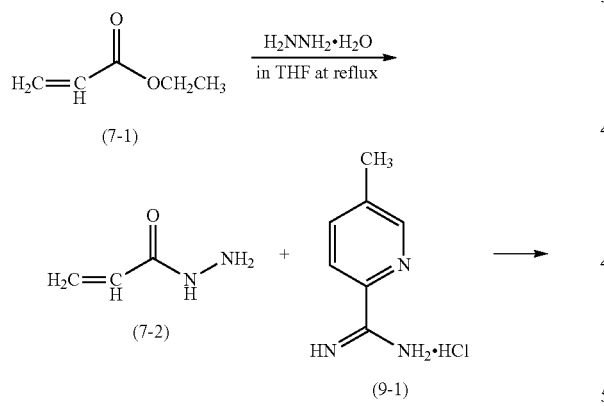

Synthesis was performed in the same manner described in the above reaction scheme 7 to purify 5-methyl-2-(3-vinyl-1H-1,2,4-triazol-5-yl)pyridine (9-2), except that 5-methylpi-colinimidamide (9-1) was added to the reaction solution containing the acrylohydrazide (7-2).

Ligand Synthesis Example 10

Synthesis of N,N-dimethyl-2-(3-vinyl-1H-1,2,4-triazol-5-yl)pyridin-4-amine

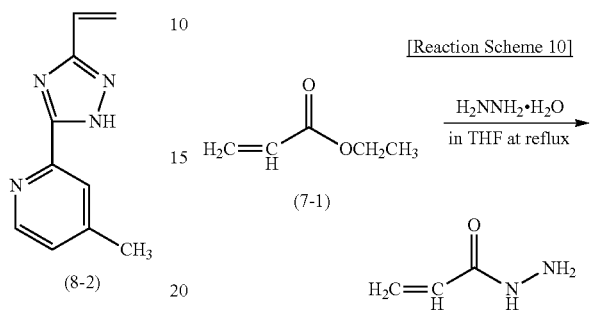

Synthesis was performed in the same manner described in the above reaction scheme 7 to purify N,N-dimethyl-2-(3-vinyl-1H-1,2,4-triazol-5-yl)pyridin-4-amine (10-2), except that 4-(dimethylamino)picolinimidamide (10-1) was added to the reaction solution containing the acrylohydrazide (7-2).

Ligand Synthesis Example 11

Synthesis of N,N-dimethyl-6-(3-vinyl-1H-1,2,4-triazol-5-yl)pyridin-3-amine

[Reaction Scheme 11]

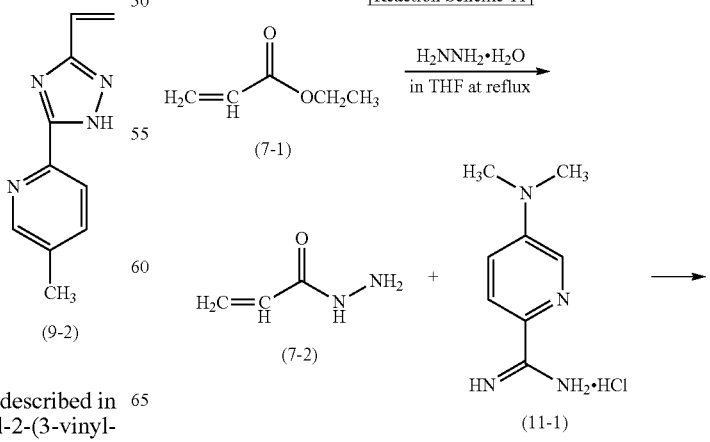

-continued

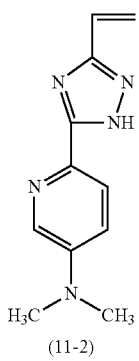
(11-2)

Synthesis was performed in the same manner described in the above reaction scheme 7 to purify N,N-dimethyl-6-(3-vinyl-1H-1,2,4-triazol-5-yl)pyridin-3-amine (11-2), except that 5-(dimethylamino)picolinimidamide (11-1) was added to the reaction solution containing the acrylohydrazide (7-2).

Ligand Synthesis Example 12

Synthesis (1) of 2-(5-(4-vinylphenyl)-4H-1,2,4-triazol-3-yl)pyridine

[Reaction Scheme 12]

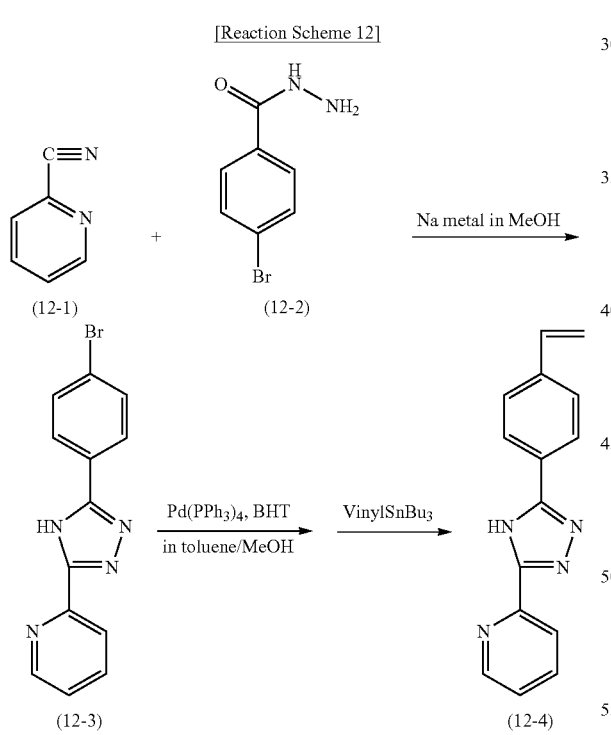

Picolinonitrile (12-1) was added to a methanol solution, in which sodium metal was dissolved, and reacted at 70° C. for 3 hours and then cooled. 4-bromobenzohydrazide (12-2) was added thereto and reacted at 70° C. for 15 minutes. Then, the temperature was lowered to 25° C. and the reaction solution was reacted for 24 hours until yellow crystals were formed. Upon completion of the reaction, the yellow crystals were collected by filtration, dissolved in ethylene glycol, and reacted at 180° C. for 3 hours. Then, the temperature of the reaction solution was lowered to room temperature, and the reaction solution was subjected to crystallization for 24 hours, thereby preparing a 2-(5-(4-bromophenyl)-4H-1,2,4-triazol-3-yl)pyridine) intermediate (12-3). After the intermediate (12-3) was added to toluene together with tetrakis(triphenylphosphine) (Pd(PPH3)4) and 2,6-di-t-butyl-4-methylphenol (BHT), tributyl(vinyl)stannane was added thereto and reacted at 80° C. for 24 hours, thereby preparing 2-(5-(4-vinylphenyl)-4H-1,2,4-triazol-3-yl)pyridine (12-4).

Figure 3:
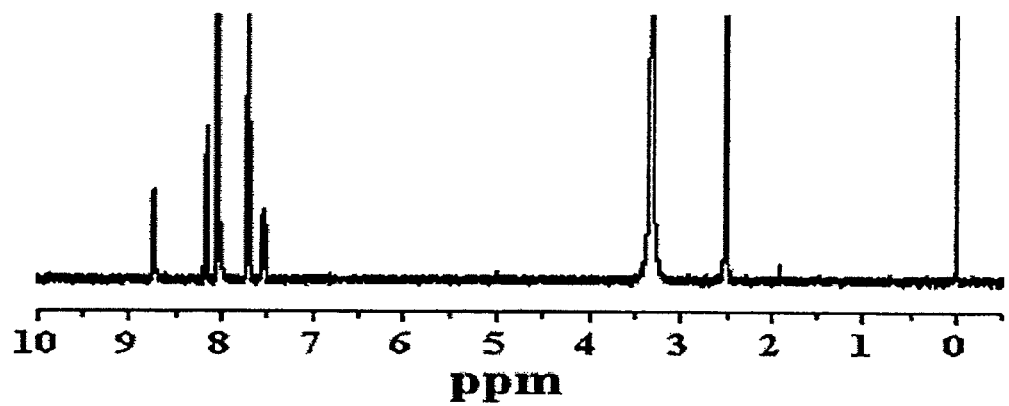
FIG. 3 shows a $^1$H-NMR spectrum of a 2-(5-(4-bromophenyl)-4H-1,2,4-triazol-3-yl)pyridine intermediate prepared by reaction scheme 12.

FIG. 3 shows the $^1$H-NMR spectrum of the 2-(5-(4-bromophenyl)-4H-1,2,4-triazol-3-yl)pyridine intermediate prepared by the above reaction scheme 12.

Figure 4:
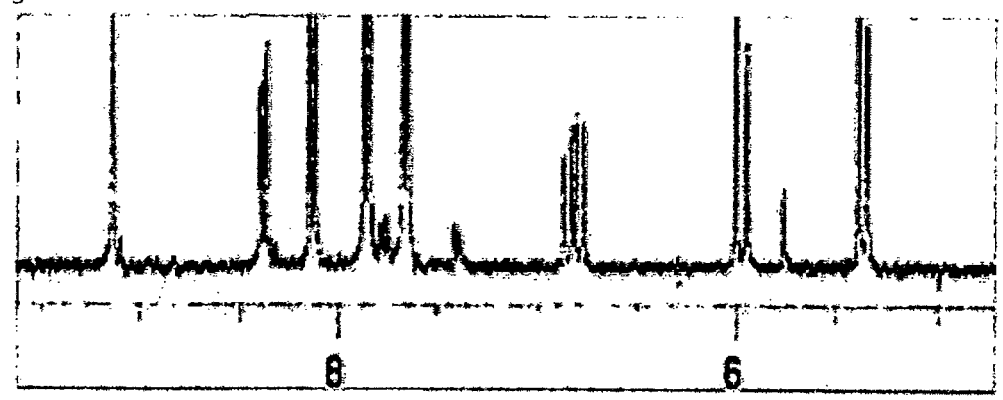
FIG. 4 shows a $^1$H-NMR spectrum of 2-(5-(4-vinylphenyl)-4H-1,2,4-triazol-3-yl)pyridine prepared by reaction scheme 12.

FIG. 4 shows the $^1$H-NMR spectrum of the 2-(5-(4-vinylphenyl)-4H-1,2,4-triazol-3-yl)pyridine prepared by the above reaction scheme 12.

Ligand Synthesis Example 13

Synthesis (2) of 2-(5-(4-vinylphenyl)-4H-1,2,4-triazol-3-yl)pyridine

[Reaction Scheme 13]

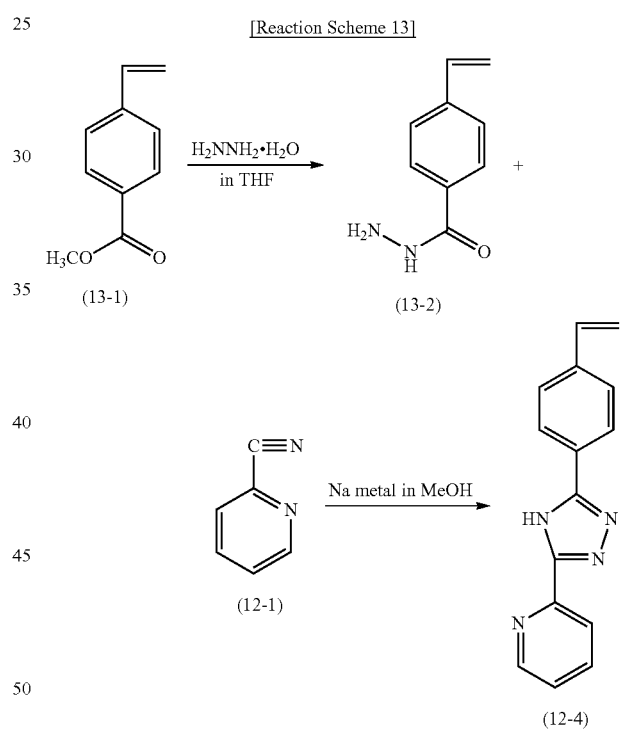

4-vinylbenzohydrazide (13-2) was prepared by dissolving methyl 4-vinylbenzoate (13-1) and hydrazine in tetrahydrofuran (THF), reacting the resulting solution at 80° C. for 1 hour, and then lowering the temperature to room temperature. Picolinonitrile (12-1) was added to a methanol solution, in which sodium metal was dissolved, and reacted at 70° C. for 3 hours and then cooled. The 4-vinylbenzohydrazide (13-2) was added to the reaction solution and reacted at 70° C. for 15 minutes. Then, the temperature was lowered to 25° C. and the reaction solution was reacted for 24 hours until yellow crystals were formed. Upon completion of the reaction, the yellow crystals were collected by filtration, dissolved in ethylene glycol, and reacted at 180° C. for 3 hours. Then, the temperature of the reaction solution was lowered to room temperature, and the reaction solution was subjected to crystallization for 24 hours, thereby preparing 2-(5-(4-vinylphenyl)-4H-1,2,4-triazol-3-yl)pyridine (12-4).

Ligand Synthesis Example 14

Synthesis-1 of 2-(5-(4-vinylphenyl)-1H-1,2,4-triazol-3-yl)pyridine

[Reaction Scheme 14]

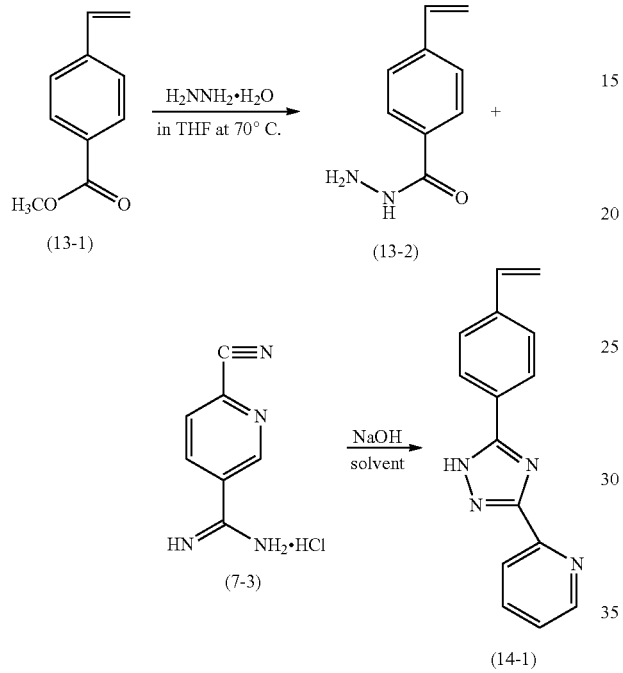

First, synthesis was performed in the same manner described in the above reaction scheme 13 to prepare 4-vinylbenzohydrazide (13-2). 2-amidino pyridine hydrochloride (7-3) and sodium hydroxide (NaOH) were added thereto and reacted at 80° C. for 1 hour, thereby preparing 2-(5-(4-vinylphenyl)-1H-1,2,4-triazol-3-yl)pyridine (14-1). After the temperature was lowered to room temperature again, the reaction was terminated with sodium hydrogen carbonate (NaHCO₃) and then extracted with ethyl acetate. Then, purification was performed by column chromatography using hexane and ethyl acetate (1:1) as a solvent.

Ligand Synthesis Example 15

Synthesis-2 of 2-(5-(4-vinylphenyl)-1H-1,2,4-triazol-3-yl)pyridine

[Reaction Scheme 15]

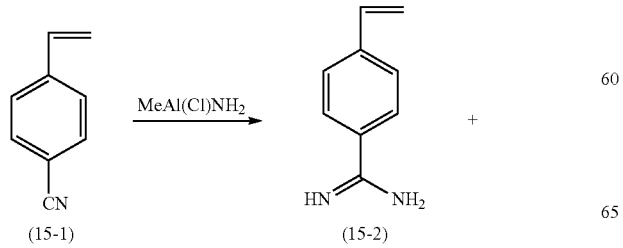

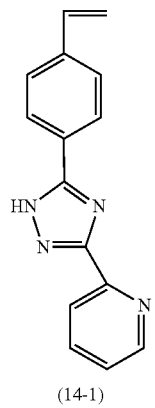

A toluene solution in which trimethylaluminum was dissolved was slowly added to an anhydrous toluene solution in which chloroammonium was dissolved in suspension to synthesize an aluminum amide reagent. Then, 4-cyanostyrene (15-1) was added thereto and reacted at 80° C. until the 4-cyanostyrene was exhausted by TLC, thereby preparing 4-vinylbenzimidamide (15-2). Next, picolinohydrazide (15-3) and sodium methoxide (NaOMe) were added thereto and reacted at 80° C. for 1 hour, thereby preparing 2-(5-(4-vinylphenyl)-1H-1,2,4-triazol-3-yl)pyridine (14-1). After the temperature was lowered to room temperature again, the reaction was terminated with sodium hydrogen carbonate (NaHCO₃) and then extracted with ethyl acetate. Then, purification was performed by column chromatography using hexane and ethyl acetate (1:1) as a solvent.

Ligand Synthesis Example 16

Synthesis of 2-(4H-1,2,4-triazol-3-yl)-5-(4-vinylphenyl)pyridine

[Reaction Scheme 16]

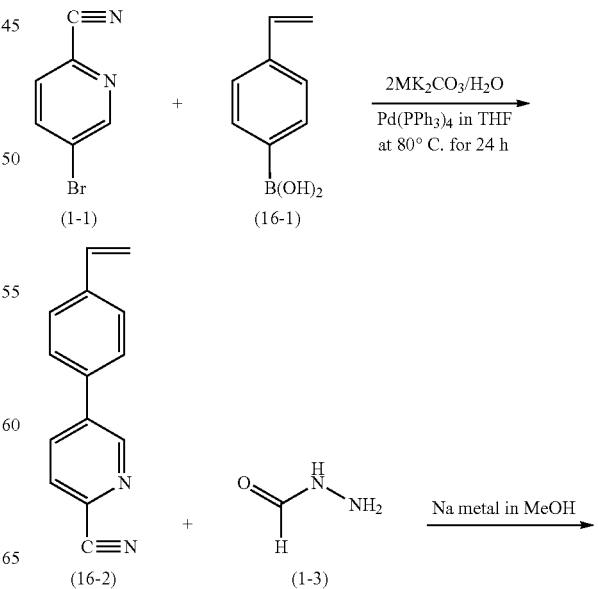

5-bromopicolinonitrile (1-1) and vinyl-phenyl boronic acid (16-1) were subjected to Suzuki coupling reaction in the presence of potassium carbonate and tetrakis(triphenylphosphine) (Pd(PPH3)4), thereby preparing a 5-(4-vinylphenyl)picolinonitrile intermediate (16-2). The intermediate (16-2) was added to a methanol solution, in which sodium metal was dissolved, and reacted at 70° C. for 3 hours. Then, the reaction solution was cooled, and formhydrazide (1-3) was added to the reaction solution and reacted at 70° C. for 15 minutes. Next, the temperature was lowered to 25° C. and the reaction solution was reacted for 24 hours until yellow crystals were formed. Upon completion of the reaction, the yellow crystals were collected by filtration, and 2-(4H-1,2,4-triazol-3-yl)-5-(4-vinylphenyl)pyridine (16-3) was purified by column chromatography using chloroform and methanol as solvents.

Figure 5:
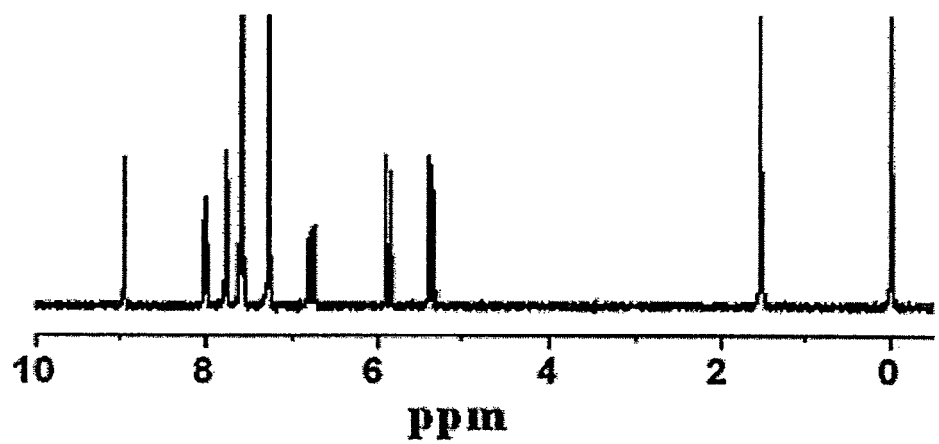
FIG. 5 shows a $^1$H-NMR spectrum of a 5-(4-vinylphenyl)picolinonitrile intermediate prepared by reaction scheme 16.

FIG. 5 shows the $^1$H-NMR spectrum of the 5-(4-vinylphenyl)picolinonitrile intermediate prepared by the above reaction scheme 16.

Figure 6:
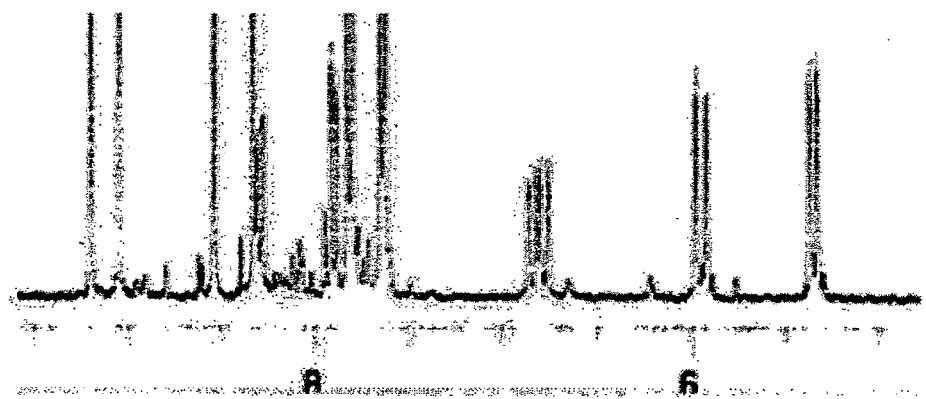
FIG. 6 shows a $^1$H-NMR spectrum of 2-(4H-1,2,4-triazol-3-yl)-5-(4-vinylphenyl)pyridine prepared by reaction scheme 16.

FIG. 6 shows the $^1$H-NMR spectrum of the 2-(4H-1,2,4-triazol-3-yl)-5-(4-vinylphenyl)pyridine prepared by the above reaction scheme 16.

Ligand Synthesis Example 17

Synthesis of 2-(5-methyl-4H-1,2,4-triazol-3-yl)-5-(4-vinylphenyl)pyridine

Synthesis was performed in the same manner described in the above reaction scheme 16 to purify 2-(5-methyl-4H-1,2,4-triazol-3-yl)-5-(4-vinylphenyl)pyridine (17-1), except that the compound that reacted with the 5-(4-vinylphenyl)picolinonitrile intermediate (16-2) was acetohydrazide (2-1).

Ligand Synthesis Example 18

Synthesis of 2-(1H-1,2,4-triazol-5-yl)-5-(4-vinylphenyl)pyridine

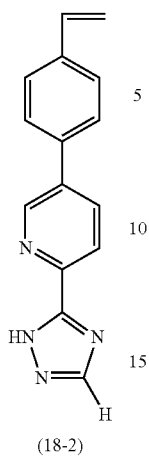

(18-2)

First, synthesis was performed in the same manner described in the above reaction scheme 16 to prepare a 5-(4-vinylphenyl)picolinonitrile intermediate (16-2). The intermediate (16-2) was added to a methanol solution, in which hydrazine was dissolved, and reacted at 25° C. to prepare 5-(4-vinylphenyl)picolinimidohydrazide (18-1). Then, the 5-(4-vinylphenyl)picolinimidohydrazide was reacted with a mixed solution of formic anhydride and formic acid (in a volume ratio of 1:1) to prepare 2-(1H-1,2,4-triazol-5-yl)-5-(4-vinylphenyl)pyridine (18-2).

Ligand Synthesis Example 19

Synthesis of 2-(3-methyl-TH-1,2,4-triazol-5-yl)-5-(4-vinylphenyl)pyridine

[Reaction Scheme 19]

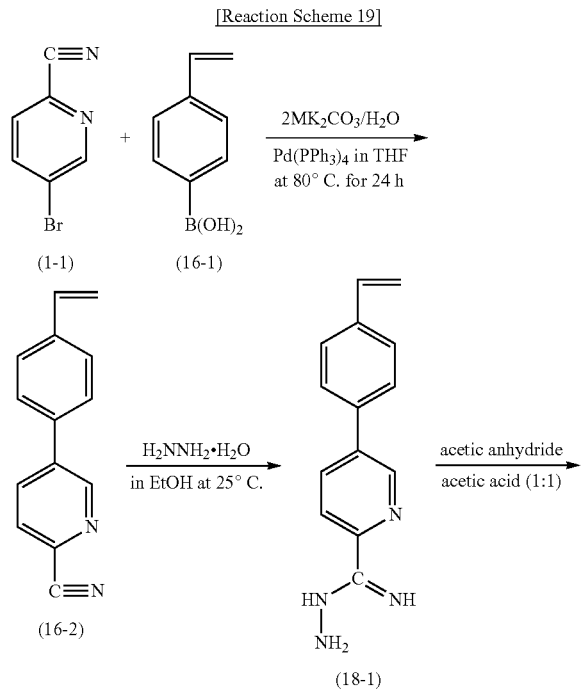

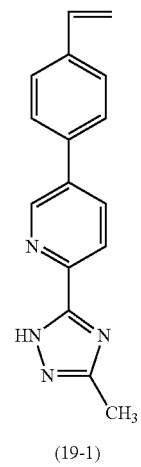

(19-1)

Synthesis was performed in the same manner described in the above reaction scheme 18 to prepare 2-(3-methyl-1H-1,2,4-triazol-5-yl)-5-(4-vinylphenyl)pyridine) (19-1), except that a mixed solution of acetic anhydride and acetic acid was used as the reaction solution.

Synthesis Example of Iridium Complex Monomer:
Synthesis of (2-(2,4-difluorophenyl)pyridine)₂(2-(5-(4-vinylphenyl)-4H-1,2,4-triazol-3-yl)pyridineiridium

[Reaction Scheme 20]

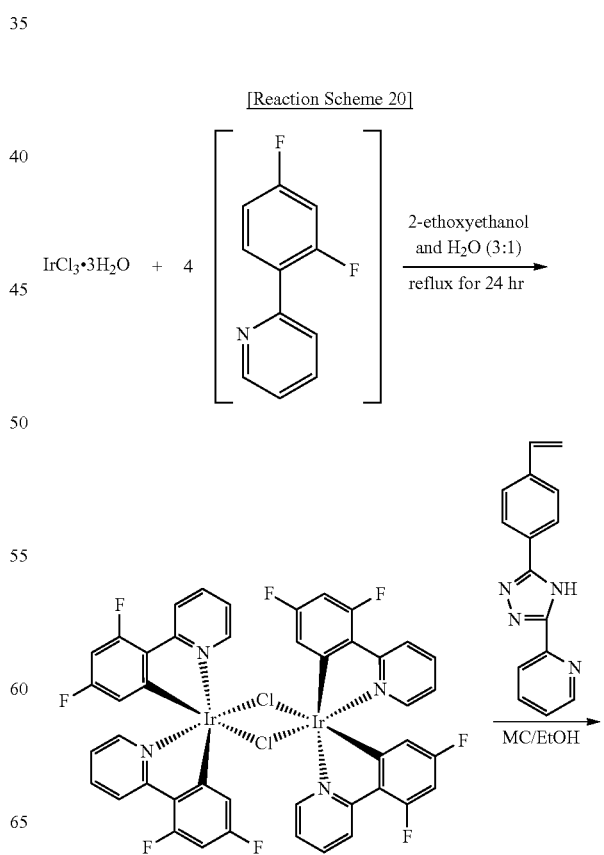

-continued

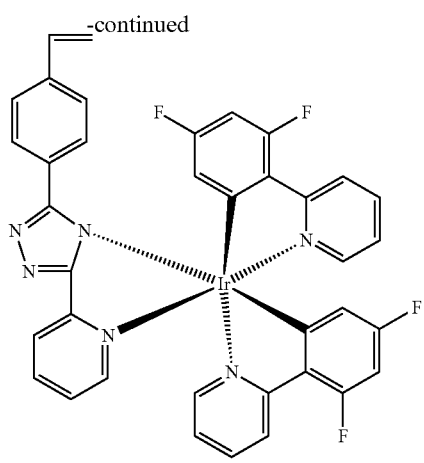

Iridium(III) chloride trihydrate (IrCl$_3$.3H$_2$O) and 2-(2,4-difluorophenyl)pyridine were added to a mixed solvent of ethoxyethanol and distilled water (in a volume ratio of 3:1) and reacted at about 130° C. to prepare tetrakis(2-(2,4-difluorophenyl)pyridine)(dichloro)diiridium. Then, the tetrakis(2-(2,4-difluorophenyl)pyridine)(dichloro)diiridium and 2-(5-(4-vinylphenyl)-4H-1,2,4-triazol-3-yl)pyridine were reacted with 2-(5-(4-vinylphenyl)-4H-1,2,4-triazol-3-yl)pyridine at about 90° C. in the presence of silver trifluoromethanesulfonate catalyst after turning off the light, thereby preparing (2-(2,4-difluorophenyl)pyridine)$_2$(2-(5-(4-vinylphenyl)-4H-1,2,4-triazol-3-yl)pyridineiridium.

Figure 7:
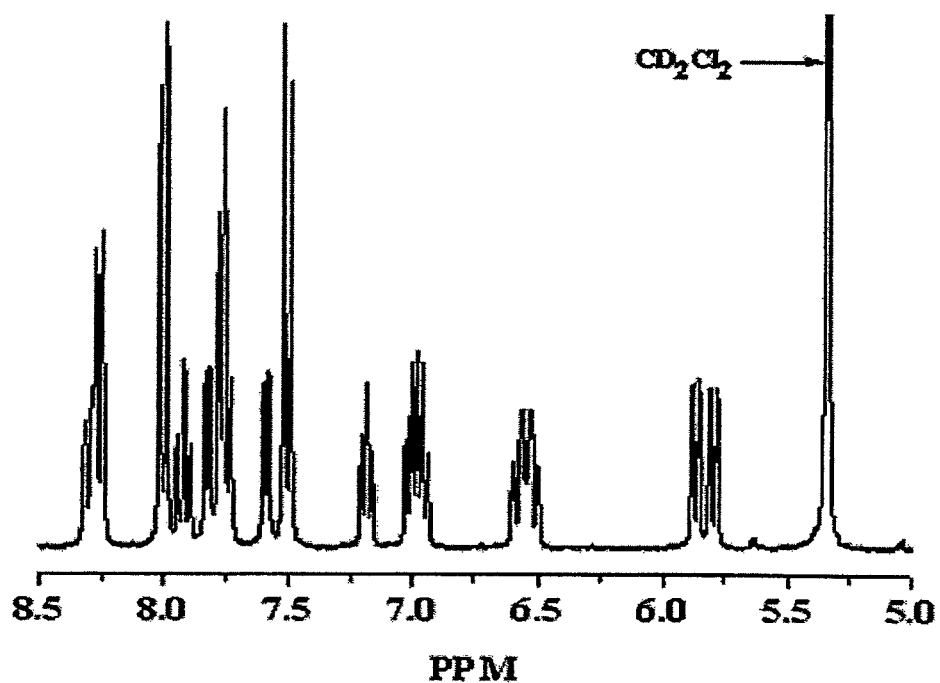
FIG. 7 shows a $^1$H-NMR spectrum of (2-(2,4-difluorophenyl)pyridine)$_2$(2-(5-(4-vinylphenyl)-4H-1,2,4-triazol-3-yl)pyridineiridium) prepared by reaction scheme 20.

FIG. 7 shows the $^1$H-NMR spectrum of the (2-(2,4-difluorophenyl)pyridine)$_2$(2-(5-(4-vinylphenyl)-4H-1,2,4-triazol-3-yl)pyridineiridium) prepared by the above reaction scheme 20.

Synthesis Example of Polymer Containing Iridium complex monomer: Synthesis of poly(9-(4-vinylphenyl)carbazole)-random-poly(iridium(2-(4H-1,2,4-triazol-3-yl)-5-vinylpyridine)(2-(2,4-difluorophenyl)pyridine)$_2$ Radical polymerization was performed at 110° C. for 24 hours, in which 9-(4-vinylphenyl)carbazole (VPC$_z$) was used as a carbazole derivative and iridium(2-(4H-1,2,4-triazol-3-yl)-5-vinylpyridine) (2-(2,4-di fluorophenyl)pyridine)$_2$ was used as an iridium complex monomer under nitrogen atmosphere by changing the content of iridium complex monomer. During the reaction, tetrahydrofuran (THF) was used as a solvent, and AIBN was used as a radical initiator. After the polymerization, methanol was added to terminate the reaction and removed by filtration. The prepared polymer was dissolved in benzene and freeze-dried, thereby preparing poly(9-(4-vinylphenyl)carbazole)-random-poly(iridium(2-(4H-1,2,4-triazol-3-yl)-5-vinylpyridine)(2-(2,4-difluorophenyl)pyridine)$_2$.

TABLE 1

| | Reactant (g) | | | Polymer | | |
|---|---|---|---|---|---|---|
| No. | AIBN | VPC$_z$ | Ir complex | NAMW (10$^3$) | MWD | F$_{Ir-complex}$ |
| 1 | 0.0020 | 0.5 | 0.01 | 31.5 | 1.47 | 1.96 |
| 2 | 0.0022 | 0.5 | 0.02 | 22.7 | 1.89 | 3.85 |
| 3 | 0.0019 | 0.5 | 0.03 | 18.3 | 2.06 | 5.66 |

VPC$_z$: Vinylphenylcarbazole
NAMW Number-Average Molecular Weight
MWD: Molecular Weight Distribution
F$_{Ir-complex}$: Content (mol %) of iridium complex in copolymer Referring to FIG. 1, the higher the content of iridium complex, the lower the number-average molecular weight, and thus the broader the molecular weight distribution. The reason for this is that when the content of large iridium complex increases, the steric hindrance that may act as a disturbing element increases, thereby limiting the formation of a polymer having a large molecular weight.

Figure 8:
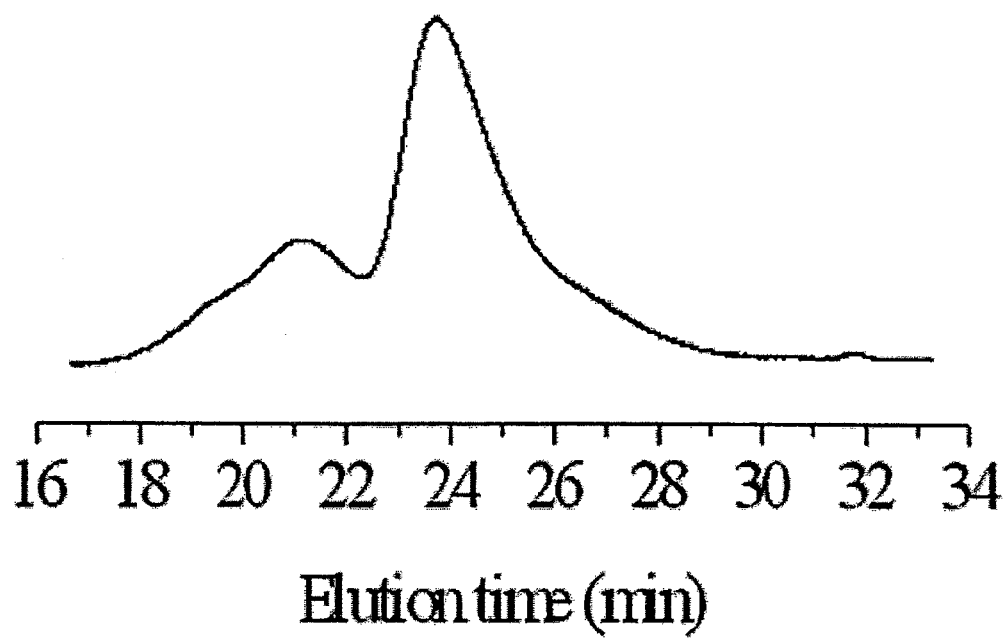
FIG. 8 shows the SEC-LS profile of the molecular weight and molecular weight distribution of a polymer (No. 1) prepared by a polymer synthesis example.

FIG. 8 shows the SEC-LS profile of the molecular weight and molecular weight distribution of the polymer (No. 1) prepared by the polymer synthesis example.

Figure 9:
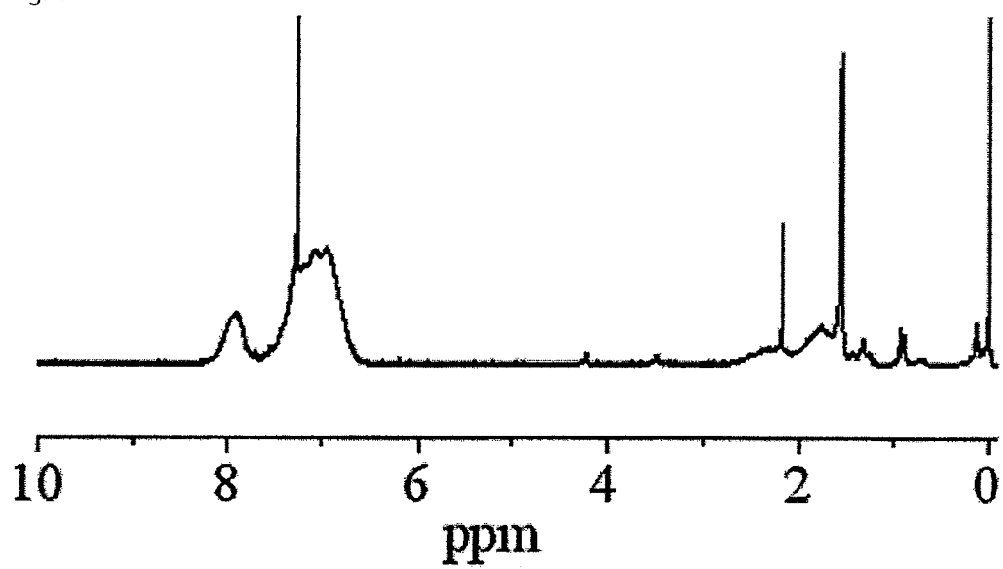
FIG. 9 shows a $^1$H-NMR spectrum of a polymer (No. 2) prepared by a polymer synthesis example.

FIG. 9 shows the $^1$H-NMR spectrum of the polymer (No. 2) prepared by the polymer synthesis example.

Analysis Example 1

Analysis of Optical Properties of Polymer Containing Iridium Complex

The polymer prepared by the polymer synthesis example was analyzed by UV-Vis spectra and photoluminescence spectra.

Figure 10:
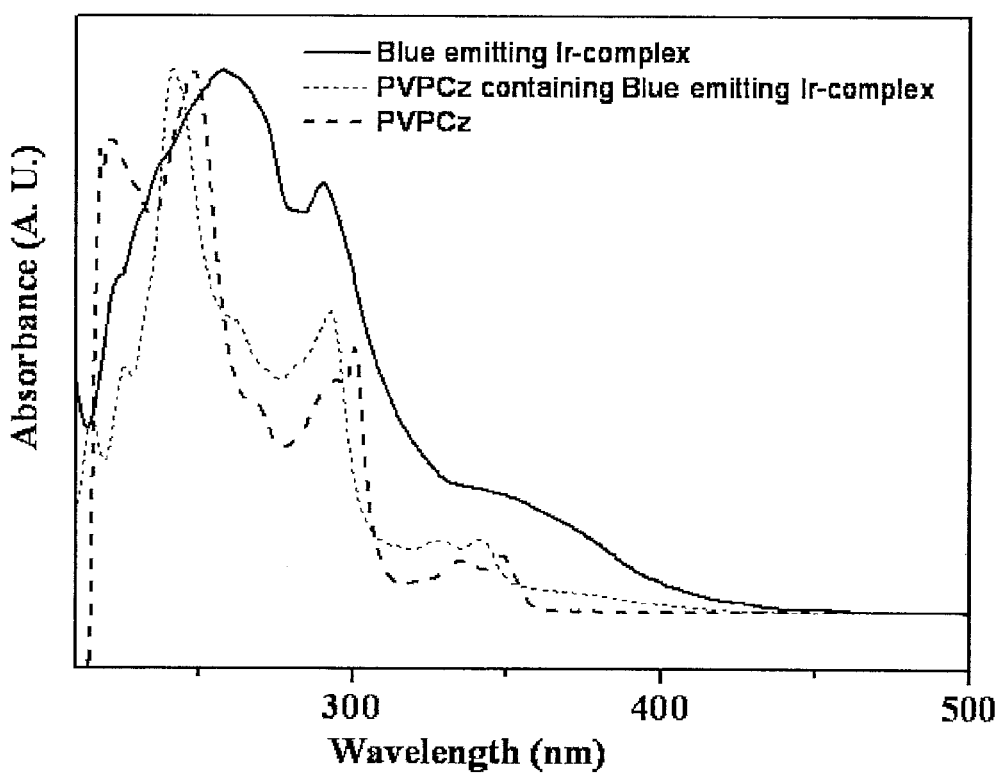
FIG. 10 shows UV-Vis spectra of a polymer prepared by a polymer synthesis example.

FIG. 10 shows the UV-Vis spectra of the polymer prepared by the polymer synthesis example.

Figure 11:
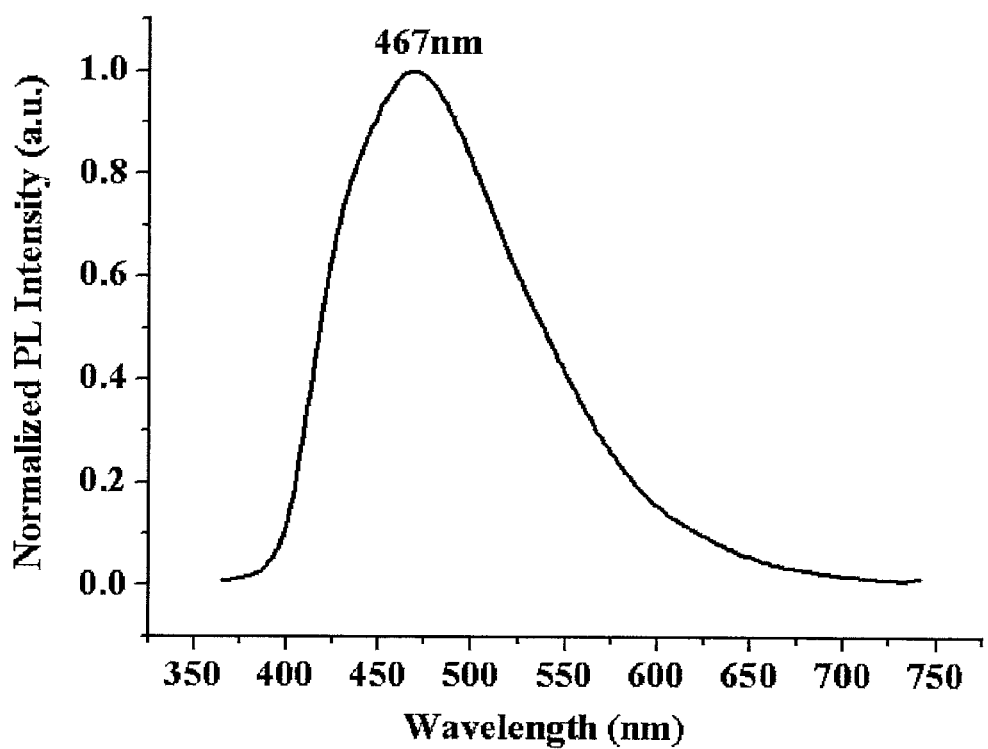
FIG. 11 shows photoluminescence spectra of a polymer prepared by a polymer synthesis example.

FIG. 11 shows the photoluminescence spectra of the polymer prepared by the polymer synthesis example.

Referring to FIG. 10, it can be seen that the metal-ligand charge transfer (MLCT) of the ligand containing iridium and phenylpyridine was observed at 345 nm. Referring to FIG. 11, it can be seen from the photoluminescence spectra, in which the maximum excited state was 345 nm, that $\lambda_{max}$ was observed at 467 nm in the blue wavelength range.

Thus, it can be understood that the polymer prepared by the polymer synthesis example is a material that can emit blue light.

According to the present invention, the polymer containing an iridium complex having both phosphorescent and fluorescent properties that exhibit blue-light emission is synthesized using a vinyl group bound to a ligand of an iridium complex monomer, and thus it is possible to improve the stability and efficiency of the light-emitting polymer. Moreover, it is possible to improve the processability and reduce the manufacturing cost by introducing the iridium complex into the vinyl-based polymer.

Example 4

Organic Electroluminescent Device

Figure 12:
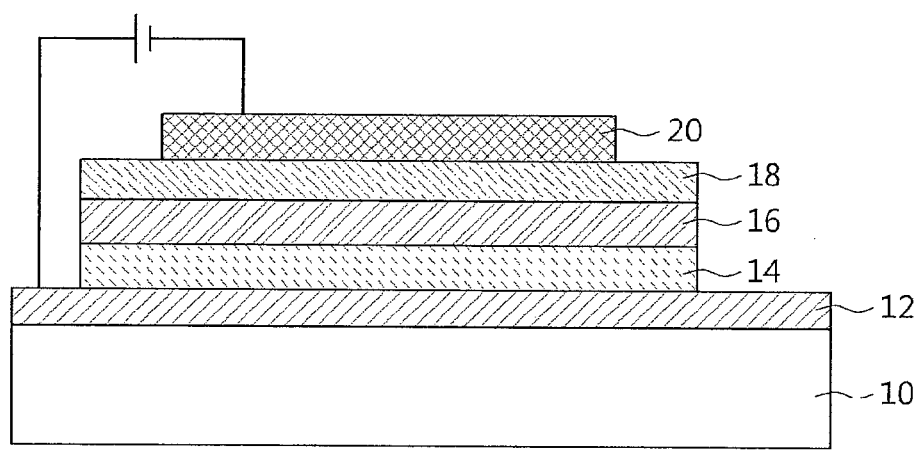
FIG. 12 is a schematic diagram showing an organic electroluminescent device according to another exemplary embodiment of the present invention.

FIG. 12 is a schematic diagram showing an organic electroluminescent device according to yet another exemplary embodiment of the present invention.

Referring to FIG. 12, the organic electroluminescent device comprises a first electrode 12 formed on a substrate 10, a second electrode 20 disposed opposite to the first electrode, and a light-emitting layer 16 interposed between the first electrode 12 and the second electrode 20. Moreover, the organic electroluminescent device may further comprise a hole transporting layer 14 disposed between the first electrode 12 and the light-emitting layer 16 and an electron transporting layer 18 disposed between the light-emitting layer 16 and the second electrode 20. The light-emitting layer 16 may comprise a blue-light emitting iridium complex represented by the above formula 1 as a dopant and a carbazole-based compound such as 4,4'-N,N'-dicarbazolbiphenyl (CBP) as a host. Otherwise, the light-emitting layer 16 may comprise a blue phosphorescent polymer containing an iridium complex and represented by the above formula 13.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

The invention claimed is:

1. An iridium complex monomer represented by the following formula 9:

[Formula 9]

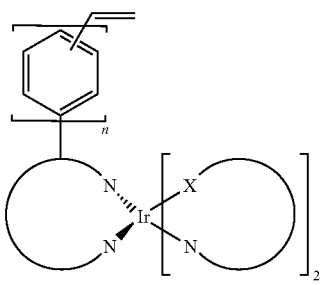

wherein in formula 9, n is an integer from 0 to 2,

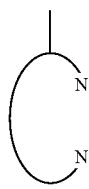

is any one selected from the group consisting of compounds represented by the following formulas 10 to 12:

[Formula 10]

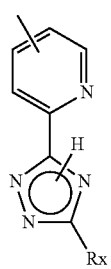

where Rx is hydrogen, a substituted or unsubstituted C1-C20 alkyl group, or a trifluoromethyl group;

[Formula 11]

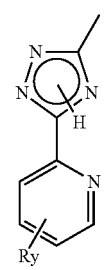

where Ry is hydrogen, a substituted or unsubstituted C1-C20 alkyl group, or an amine group (—NR'R", where R' and R" are, independently from each other, hydrogen or a C1-C20 alkyl group); and

[Formula 12]

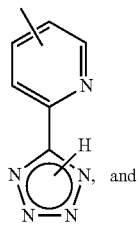

, and

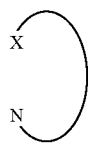

is any one selected from the group consisting of compounds represented by the following formulas 6 to 8:

[Formula 6]

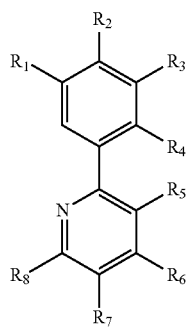

where R1 to R4 are, independently from each other, a fluorine group or a cyano group, and R5 to R8 are, independently from each other, hydrogen, a substituted or unsubstituted C1-C20 alkyl group, a substituted or unsubstituted C1-C20 alkoxy group, or an amine group (—NR'R", where R' and R" are, independently from each other, hydrogen or a C1-C20 alkyl group);

[Formula 7]

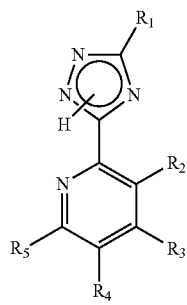

where R1 is hydrogen, a substituted or unsubstituted C1-C20 alkyl group, or a trifluoromethyl group, and R2 to R5 are, independently from each other, hydrogen, a substituted or unsubstituted C1-C20 alkyl group, a substituted or unsubstituted C1-C20 alkoxy group, or an amine group (—NR'R", where R' and R" are, independently from each other, hydrogen or a C1-C20 alkyl group); and

[Formula 8]

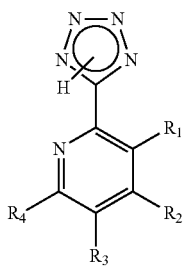

where R1 to R4 are, independently from each other, hydrogen, a substituted or unsubstituted C1-C20 alkyl group, a substituted or unsubstituted C1-C20 alkoxy group, or an amine group (—NR'R", where R' and R" are, independently from each other, hydrogen or a C1-C20 alkyl group).

2. A phosphorescent polymer represented by the following formula 13:

[Formula 13]

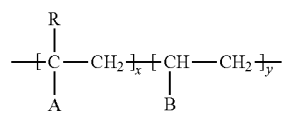

wherein in formula 13, R is hydrogen or a substituted or unsubstituted C1-C20 alkyl group, $2 \leq x+y \leq 100$, and y is an integer from 1 to 99, A is any one selected from the group consisting of carbazole derivatives represented by the following formulas 14 to 17, and B is an iridium complex represented by the following formula 18:

[Formula 14]

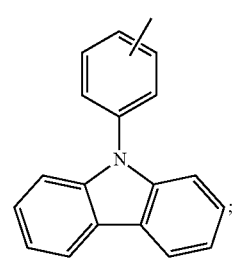

[Formula 15]

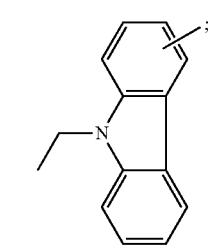

[Formula 16]

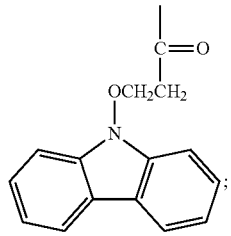

[Formula 17]

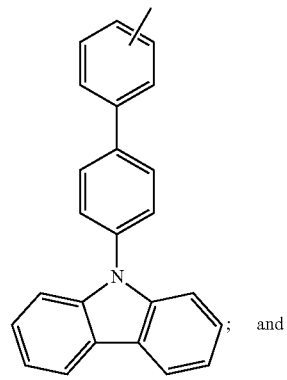
; and

[Formula 18]

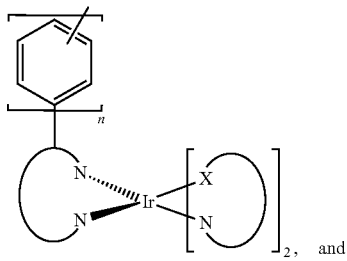
, and wherein in formula 18, n is an integer from 0 to 2,

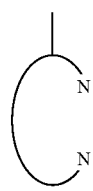

is any one selected from the group consisting of compounds represented by the following formulas 10 to 12:

[Formula 10]

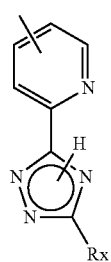

where Rx is hydrogen, a substituted or unsubstituted C1-C20 alkyl group, or a trifluoromethyl group;

[Formula 11]

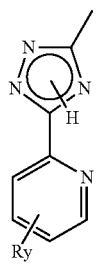

where Ry is hydrogen, a substituted or unsubstituted C1-C20 alkyl group, or an amine group (—NR'R", where R' and R" are, independently from each other, hydrogen or a C1-C20 alkyl group); and

[Formula 12]

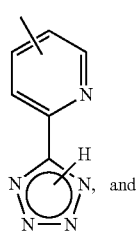

and

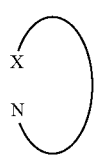

is any one selected from the group consisting of compounds represented by the following formulas 6 to 8:

[Formula 6]

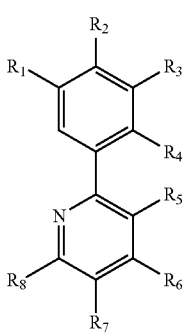

where R1 to R4 are, independently from each other, a fluorine group or a cyano group, and R5 to R8 are, independently from each other, hydrogen, a substituted or unsubstituted C1-C20 alkyl group, a substituted or unsubstituted C1-C20 alkoxy group, or an amine group (—NR'R", where R' and R" are, independently from each other, hydrogen or a C1-C20 alkyl group);

[Formula 7]

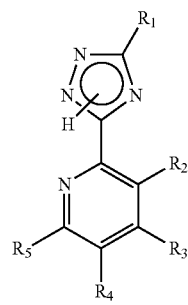

where R1 is hydrogen, a substituted or unsubstituted C1-C20 alkyl group, or a trifluoromethyl group, and R2 to R5 are, independently from each other, hydrogen, a substituted or unsubstituted C1-C20 alkyl group, a substituted or unsubstituted C1-C20 alkoxy group, or an amine group (—NR'R", where R' and R" are, independently from each other, hydrogen or a C1-C20 alkyl group); and

[Formula 8]

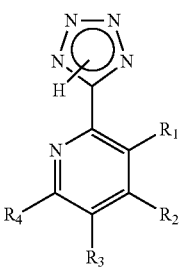

where R1 to R4 are, independently from each other, hydrogen, a substituted or unsubstituted C1-C20 alkyl group, a substituted or unsubstituted C1-C20 alkoxy group, or an amine group (—NR'R", where R' and R" are, independently from each other, hydrogen or a C1-C20 alkyl group).

3. An organic electroluminescent device comprising:
a first electrode;
a second electrode disposed opposite to the first electrode; and
a light-emitting layer interposed between the first electrode and the second electrode,
wherein the light-emitting layer comprises the phosphorescent polymer of claim 2.

4. The organic electroluminescent device of claim 3, further comprising at least one of a hole transporting layer disposed between the first electrode and the light-emitting layer and an electron transporting layer disposed between the light-emitting layer and the second electrode.

* * * * *